United States Patent [19]

Pavan et al.

[11] 4,257,976

[45] Mar. 24, 1981

[54] RESOLUTION PROCESS USING L OR D N-METHYL-EPHEDRINE

[75] Inventors: Charles Pavan, Nogent-sur-Marne; Jacques Bulidon, Paris, both of France

[73] Assignee: Roussel Uclaf, Paris, France

[21] Appl. No.: 96,028

[22] Filed: Nov. 20, 1979

[30] Foreign Application Priority Data

Dec. 8, 1978 [FR] France .................. 78 34591

[51] Int. Cl.³ .................. C07C 61/37; C07B 19/00
[52] U.S. Cl. .................. 260/501.17; 562/401; 562/506
[58] Field of Search .................. 562/401, 506; 260/501.17

[56] References Cited

U.S. PATENT DOCUMENTS

| 3,646,118 | 2/1972 | Goffinet et al. | 562/401 |
| 3,666,798 | 5/1972 | Matsui et al. | 562/401 |
| 3,739,019 | 6/1973 | Ueda et al. | 562/401 |
| 3,842,125 | 10/1974 | Horiuchi et al. | 562/401 |
| 3,879,451 | 4/1975 | Yoshioka et al. | 562/401 |

FOREIGN PATENT DOCUMENTS

1178423 1/1970 United Kingdom .................. 562/50

*Primary Examiner*—Natalie Trousof
*Assistant Examiner*—Vera C. Clarke
*Attorney, Agent, or Firm*—Hammond & Littell, Weissenberger and Muserlian

[57] ABSTRACT

A process for the resolution of DL-cis chrysanthemic acid or DL-trans chrysanthemic acid with L or D N-methyl-ephedrine to form the corresponding salt and acid hydrolyzing the same which resolved acids are intermediates for preparing esters having a remarkable insecticidal activity.

9 Claims, No Drawings

RESOLUTION PROCESS USING L OR D N-METHYL-EPHEDRINE

STATE OF THE ART

Various processes for the resolution of DL-trans chrysanthemic acid are described in French Pat. No. 1,536,458 and patent of addition No. 92,748, British Pat. No. 1,178,423 and Campbell [J.Sci. Food Agr., Vol. 2 (1951), p. 421]. Processes for the resolution of DL-cis chrysanthemic acid are described by the said Campbell reference and Katsuhidi et al [Agr. Biol. Chem., Vol. 37 (10), 1973, p. 2235-40]. Also pertinent is British Pat. No. 1,394,170. Most of the processes use relatively costly reactants such as quinine or reactants not commercially available.

OBJECTS OF THE INVENTION

It is an object of the invention to provide an easily commercialized process for the resolution of DL-cis or DL-trans chrysanthemic acids with commercially available, relatively inexpensive solvents and reactants.

This and other objects and advantages of the invention will become obvious from the following detailed description.

THE INVENTION

The novel process of the invention for the resolution of DL-cis or DL-trans chrysanthemic acid comprises reacting DL-cis of DL-trans chrysanthemic acid with D or L N-methyl-ephedrine in an organic solvent, recovering the crystallized salt of L N-methyl-ephedrine and D-cis or D-trans chrysanthemic acid or D N-methyl-ephedrine and L-cis or L-trans chrysanthemic acid and subjecting the recovered salt to acid hydrolysis to obtain the corresponding D-cis or D-trans chrysanthemic acid or L-trans or L-cis chrysanthemic acid.

In the process of the invention for the resolution of DL-cis chrysanthemic acid, the said acid is reacted with L- or D N-methyl-ephedrine in an organic solvent, the resulting salt of L N-methyl-ephedrine and D-cis chrysanthemic acid or D N-methyl-ephedrine and L-cis chrysanthemic acid which crystallizes is recovered and subjected to acid hydrolysis to obtain L-cis or D-cis chrysanthemic acid.

Preferably, the organic solvent used in the said salification is selected from the group consisting of toluene, ethyl acetate, acetone, isopropanol and isopropyl ether, especially isopropyl ether and the reaction mixture is heated just to reflux to obtain total dissolution of N-methyl-ephedrine and is slowly cooled to room temperature and then cooled to about $-10°$ C. The salt may be recovered by vacuum filtration and the acid hydrolysis is preferably effected with hydrochloric acid in methylene chloride or isopropyl ether.

The preferred process for the resolution of Dl-trans chrysanthemic acid comprises reacting the said acid with L or D N-methyl-ephedrine in an organic solvent, recovering the resulting salt of L N-methyl-ephedrine and D-trans chrysanthemate or D N-methyl-ephedrine and L-trans chrysanthemic acid which crystallizes and subjecting the latter to acid hydrolysis to obtain D-trans or L-trans chrysanthemic acid.

Preferably, the said salification is effected in ethyl acetate, toluene or isopropyl ether and the mixture is heated to about $40°-45°$ C. to effect complete dissolution of N-methyl-ephedrine and then slowly cooling the mixture to room temperature followed by cooling to $0°$ C. The acid hydrolysis is preferably effected with hydrochloric acid in methylene chloride or isopropyl ether.

As a modification of the process of the invention, the mother liquor of crystallization containing the non-crystallized salt of N-methyl-ephedrine and chrysanthemic acid may be evaporated to dryness and the resulting salt may be subjected to acid hydrolysis to obtain the corresponding chrysanthemic acid.

The resolution base used in the process can be easily recovered after the acid hydrolysis by known processes.

In the following examples there are described several preferred embodiments to illustrate the invention. However, it should be understood that the invention is not intended to be limited to the specific embodiments.

EXAMPLE 1

D-cis-chrysanthemic acid

STEP A: L N-methyl-ephedrine D-cis chrysanthemate 16 g of L N-methyl-ephedrine were added at $20°$ C. to a mixture of 15 g of DL-cis chrysanthemic acid in 75 ml of toluene and the mixture was heated to $60°$ C. and allowed to cool to $20°$ C. The mixture was held at $20°$ C. for 48 hours and was then vacuum filtered. The recovered product was washed with toluene to obtain L N-methyl-ephedrine D-cis chrysanthemate which was used as is for the next step.

STEP B: D-cis chrysanthemic acid

The salt of Step A was added to a mixture of 7.5 ml of isopropyl ether and 19.5 ml of aqueous 2N hydrochloric acid and the mixture was stirred for 30 minutes and was decanted. The aqueous phase was extracted with isopropyl ether and the combined organic phases were washed with water, dried and evaporated to dryness under reduced pressure to obtain 4.5 g of D-cis chrysanthemic acid with a specific rotation of $[\alpha]_D^{20} = +65.5°$ (c=2% in dimethylformamide). The product was about 94% of D-cis isomer and about 6% of L cis isomer.

In an analogous manner, D N-methyl-ephedrine and DL-cis chrysanthemic acid were reacted to obtain D N-methyl-ephedrine L-cis chrysanthemate which was then reacted to obtain L-cis chrysanthemic acid with a specific rotation of $[\alpha]_D^{20} = -65.5°$ (c=2% in dimethylformamide).

EXAMPLE 2

D-cis chrysanthemic acid

STEP A: L N-methyl-ephedrine D-cis chrysanthemate

Using the procedure of Step A of Example 1, 50 g of DL-cis chrysanthemic acid, 125 ml of toluene and 53.3 g of L N-methyl-ephedrine and was heated to reflux and allowed to cool to $20°$ C. in 7 hours with gentle stirring. The mixture was then cooled to $0°$ C. for 4 hours and was vacuum filtered. The recovered product was washed with toluene at $0°$ C. to obtain L N-methyl-ephedrine D-cis chrysanthemate which was used as is for the next step.

STEP B: D-cis chrysanthemic acid

The salt of Step A was dissolved in 100 ml of methylene chloride and 100 ml of aqueous 2N hydrochloric acid and the mixture was stirred at $20°$ C. for 30 minutes and was decanted. The organic phase was washed with water and the aqueous phases were extracted with methylene chloride. The combined organic phases were evaporated to dryness under reduced pressure to obtain 20.5 g of D-cis chrysanthemic acid with a specific rotation of $[\alpha]_D^{20} = +69.5°$ C. (c=2% in dimethylformamide). The product contained about 96.4% of the D-cis acid and about 3.6% of the L-cis acid.

EXAMPLE 3

The procedure of Step A of Example 2 was repeated using 125 ml of ethyl acetate in place of toluene to obtain L N-methyl-ephedrine D-cis chrysanthemate. The latter was treated as in Step B of Example 2 to obtain 17.6 g of D-cis chrysanthemic acid with a specific rotation of $[\alpha]_D^{20} = +67.5°$ (c=2% in dimethylformamide). The product was about 95% of D-cis acid and about 5% of L-cis acid.

EXAMPLE 4

The procedure of Step A of Example 2 was repeated with 100 ml of acetone in place of toluene and the mixture was cooled and vacuum filtered to 20° C. rather than 0° C. to obtain L N-methyl-ephedrine D-cis chrysanthemate. The said salt was treated by the procedure of Step B of Example 2 to obtain 14.8 g of D-cis chrysanthemic acid with a specific rotation of $[\alpha]_D^{20} = +71°$ (c=2% in dimethylformamide). The product contained about 97.3% of the D-cis acid and about 2.7% of the L-cis acid.

EXAMPLE 5

The procedure of Step A was repeated with 125 ml of isopropanol in place of toluene and the mixture was cooled and vacuum filtered at −10° C. instead of 0° C. to obtain L N-methyl-ephedrine D-cis chrysanthemic acid. The said salt was treated as in Step B of Example 2 to obtain 16 g of D-cis chrysanthemic acid with a specific rotation of $[\alpha]_D^{20} = +69°$ (c=2% in dimethylformamide). The product contained about 96% of the D-cis acid and about 4% of the L-cis acid.

EXAMPLE 6

The procedure of Step A of Example 2 was repeated with 125 ml of isopropyl ether in place of toluene and the mixture was cooled to and vacuum filtered at 20° C. rather than 0° C. to obtain L N-methyl-ephedrine D-cis chrysanthemate. The said salt was treated as in Step B of Example 2 to obtain 20.45 g of D-cis chrystanthemic acid with a specific rotation of $[\alpha]_D^{20} = +73.5°$ (c=2% in dimethylformamide). The product contained about 99% of D-cis acid and about 1% of the L-cis acid.

EXAMPLE 7

L-trans Chrysanthemic Acid

STEP A: D N-methyl-ephedrine L-trans chrysanthemate 40 g of DL-trans chrysanthemic acid with a specific rotation of $[\alpha]_D^{20} = 0°$ (c=5% in dimethylformamide) were added to 80 ml of isopropyl ether and then 40.4 g of D N-methyl-ephedrine with a melting point of 87° C. and a specific rotation of $[\alpha]_D^{20} = +29.50°$ (c=4% in methanol) were added thereto all at once at 20° C. The mixture was heated to about 40°–45° C. until complete dissolution occured and the mixture was regularly cooled over 3 hours to 20° C. The mixture was seeded near 35° C. with 0.2 g of D N-methyl-ephedrine L-trans chrysanthemate. The mixture was regularly cooled over 4 hours to 0° C. and was held at 0° C. for one hour and was vacuum filtered. The recovered product was washed with isopropyl ether at 0° C. and was dried under reduced pressure at 20° C. to obtain 31.8 g of D N-methyl-ephedrine L-trans chrysanthemate which was used as is for the next step.

STEP B: L-trans chrysanthemic acid 31.8 g of the salt of Step B were added at 20° C. to a mixture of 41.6 ml of water, 10.4 ml of aqueous 22° Be hydrochloric acid and 20 ml of isopropyl ether and the mixture was stirred for 30 minutes. The pH was verified and if necessary the pH was adjusted by addition of aqueous hydrochloric acid. The mixture stood for 15 minutes and was then decanted. The aqueous phase was extracted with isopropyl ether and the combined organic phases were washed with a mixture of water and hydrochloric acid with a pH of 1.5–2. The decanted organic phase was then washed with water and the two aqueous phases were extracted with isopropyl ether. The combined organic phases were washed 4 times with water and the wash waters were extracted with isopropyl ether. The combined organic phases were evaporated to dryness under reduced pressure to obtain 14.4 g of L-trans chrysanthemic acid with a specific rotation of $[\alpha]_D^{20} = -35°$ (c=5% in dimethylformamide) and having an acid No. of 334 (333 theoretical). The product contained about 96% of L-trans acid and about 4% of D-trans acid.

In an analogous manner, L N-methyl-ephedrine and DL trans chrysanthemic acid were reacted to obtain L N-methyl-ephedrine D-trans chrysanthemate which was then reacted to obtain D-trans chrysanthemic acid with a specific rotation of $[\alpha]_D^{20} = +35°$ (c=5% in dimethylformamide).

The D N-methyl-ephedrine salt used for the seeding in Step A was prepared by warming a mixture of 1.7 g of L-trans chrysanthemic acid, 1.8 g of DN-methyl-ephedrine and 3.4 ml of toluene to 60° C. and then cooling the mixture with stirring to 20° C. over 3 hours. The mixture was held at 20° C. for 16 hours and was then vacuum filtered. The recovered salt was washed with toluene and dried to obtain 1.7 g of the said salt.

Various modifications of the process of the invention may be made without departing from the spirit or scope thereof and it is to be understood that the invention is intended to be limited only as defined in the appended claims.

We claim:

1. A process for the resolution of DL-cis or DL-trans chrysanthemic acids comprises reacting DL-cis or DL-trans chrysanthemic acid with D or L N-methyl-ephedrine in an organic solvent, recovering the crystallized salt of LN-methyl-ephedrine and D-cis or D-trans chrysanthemic acid or DN-methyl-ephedrine and L-cis or L-trans chrysanthemic acid and recovering from the salt the corresponding resolved chrysanthemic acid.

2. The process of claim 1 wherein DL-cis chrysanthemic acid is reacted with L or D N-methyl-ephedrine, the salt of L N-methyl-ephedrine D-cis chrysanthemic acid or D N-methyl-ephedrine and L-cis chrysanthemic acid crystallizes and D-cis chrysanthemic acid or L-cis chrysanthemic acid is recovered.

3. The process of claim 2 wherein the solvent is selected from the group consisting of toluene, ethyl acetate, acetone, isopropanol and isopropyl ether.

4. The process of claim 2 wherein the solvent is isopropyl ether.

5. The process of claim 2 wherein the solvent is toluene.

6. The process of claim 1 wherein DL-trans chrysanthemic acid is reacted with L or D N-methyl-ephedrine, the salt of L N-methyl-ephedrine and D-trans chrysanthemic acid or D N-methyl-ephedrine and L-trans chrysanthemic acid crystallizes and D-trans chrysanthemic acid or L-trans chrysanthemic acid is recovered.

7. The process of claim 6 wherein the organic solvent is toluene or isopropyl ether.

8. The process of claim 1 wherein the mother liquors of crystallization are evaporated to dryness to obtain the non-crystallizing salt of N-methyl-ephedrine and chrysanthemic acid and recovering from the said salt the corresponding resolved chrysanthemic acid.

9. A compound selected from the group consisting of D N-methyl-ephedrine L-trans chrysanthemate, L N-methyl-ephedrine D-trans chrysanthemate, L N-methyl-ephedrine D-cis chrysanthemate and D N-methyl-ephedrine L-cis chrysanthemate.

* * * * *